United States Patent
Legrand et al.

(10) Patent No.: US 6,379,401 B1
(45) Date of Patent: Apr. 30, 2002

(54) ANHYDROUS COMPOSITION FOR BLEACHING KERATIN FIBERS COMPRISING A COMBINATION OF A WATER-SOLUBLE THICKENING POLYMER AND A NONIONIC AMPHIPHILIC POLYMER COMPRISING AT LEAST ONE FATTY CHAIN

(75) Inventors: Frédéric Legrand, Boulogne Billancourt; Jean Millequant, Saint Maur, both of (FR)

(73) Assignee: L'Oreal, S.A., Paris (FR)

(*) Notice: Subject to any disclaimer, the term of this patent is extended or adjusted under 35 U.S.C. 154(b) by 0 days.

(21) Appl. No.: 09/492,779

(22) Filed: Jan. 28, 2000

(30) Foreign Application Priority Data

Jan. 29, 1999 (FR) .............................. 99 01056

(51) Int. Cl.$^7$ .................................. A61K 7/13

(52) U.S. Cl. .................... 8/431; 8/431; 8/111; 8/101; 8/552; 8/553; 8/557; 8/561; 8/405

(58) Field of Search ............................. 8/431, 111, 101, 8/552, 553, 557, 561, 405

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/567.6 |
| 2,528,378 A | 10/1950 | Mannheimer | 260/309.6 |
| 2,781,354 A | 2/1957 | Mannheimer | 260/309.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,632,559 A | 1/1972 | Matter et al. | 260/78 |
| 3,874,870 A | 4/1975 | Green et al. | 71/67 |
| 3,912,808 A | 10/1975 | Sokol | 424/71 |
| 3,915,921 A | 10/1975 | Schlatzer, Jr. | 260/174 |
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/66 |
| 4,001,432 A | 1/1977 | Green et al. | 424/329 |
| 4,005,193 A | 1/1977 | Green et al. | 424/168 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567 |
| 4,027,020 A | 5/1977 | Green et al. | 424/248.56 |
| 4,031,307 A | 6/1977 | DeMartino et al. | 536/114 |
| 4,131,576 A | 12/1978 | Iovine et al. | 260/17.4 |
| 4,165,367 A | 8/1979 | Chakrabarti | 424/47 |
| 4,170,637 A | 10/1979 | Pum | 424/62 |
| 4,197,865 A | 4/1980 | Jacquet et al. | 132/7 |
| 4,327,751 A * | 5/1982 | Evans et al. | 424/62 |
| 4,349,532 A | 9/1982 | Vanlerberghe et al. | 424/47 |
| 4,390,689 A | 6/1983 | Jacquet et al. | 528/335 |
| 4,509,949 A | 4/1985 | Huang et al. | 586/558 |
| 4,702,906 A | 10/1987 | Jacquet et al. | 424/70 |
| 4,719,282 A | 1/1988 | Nadolsky et al. | 528/310 |
| 4,839,166 A | 6/1989 | Grollier et al. | 424/71 |
| 4,996,059 A | 2/1991 | Grollier et al. | 424/71 |
| 5,089,252 A | 2/1992 | Grollier et al. | 424/47 |
| 5,674,476 A | 10/1997 | Clausen et al. | 424/62 |
| 5,783,175 A * | 7/1998 | Schultz et al. | 424/62 |
| 5,888,484 A | 3/1999 | Schmitt et al. | 424/62 |
| 6,132,707 A * | 10/2000 | Dubief et al. | 424/70.08 |
| 6,180,118 B1 * | 1/2001 | Maubru et al. | 424/401 |

FOREIGN PATENT DOCUMENTS

| | | |
|---|---|---|
| DE | 38 14 356 | 9/1988 |
| DE | 38 44 956 | 9/1988 |
| DE | 197 23 538 | 9/1998 |
| EP | 0 080 976 | 6/1983 |
| EP | 0 216 479 | 4/1987 |
| EP | 0 337 354 | 10/1989 |
| EP | 0 557 203 | 8/1993 |
| EP | 0 650 719 | 5/1995 |
| EP | 0 778 020 | 6/1997 |
| EP | 0 827 738 | 3/1998 |
| FR | 1 400 366 | 12/1965 |

(List continued on next page.)

OTHER PUBLICATIONS

English language Derwent Abstract of DE 38 14 356. Sep. 1998.
English language Derwent Abstract of DE 38 44 956. Mar. 1996.
English language Derwent Abstract of DE 197 23 538. Sep. 1998.
English language Derwent Abstract of EP 0 080 976. Jun. 1983.
English language Derwent Abstract of EP 0 557 203. Aug. 1993.
English language Derwent Abstract of EP 0 827 738. Mar. 1998.
English language Derwent Abstract of FR 2 077 143. No Date.
English language Derwent Abstract of FR 2 080 759. No date.
English language Derwent Abstract of FR 2 252 840. Aug. 1975.

(List continued on next page.)

*Primary Examiner*—Necholus Ogden
*Assistant Examiner*—Eisa Elhilo
(74) *Attorney, Agent, or Firm*—Finnegan Henderson Farabow Garrett & Dunner, L.L.P.

(57) ABSTRACT

The present invention relates to anhydrous compositions for bleaching keratin fibers, in particular human keratin fibers, containing at least one alkaline agent, at least one peroxygenated salt, at least one water-soluble thickening polymer, and at least one nonionic amphiphilic polymer including at least one fatty chain, to the use of these compositions to prepare ready-to-use bleaching compositions by mixing with an aqueous hydrogen peroxide composition, and to a process for bleaching the hair using these anhydrous compositions.

49 Claims, No Drawings

FOREIGN PATENT DOCUMENTS

| | | |
|---|---|---|
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 519 863 | 7/1983 |
| FR | 2 598 611 | 11/1987 |
| FR | 2 633 940 | 1/1990 |
| FR | 2 769 221 | 4/1999 |
| WO | WO 92/03120 | 3/1992 |
| WO | WO 98/03150 | 1/1998 |

OTHER PUBLICATIONS

English language Derwent Abstract of FR 2 270 846. Jan. 1976.

English language Derwent Abstract of FR 2 280 361. Apr. 1976.

English language Derwent Abstract of FR 2 320 330. Apr. 1977.

English language Derwent Abstract of FR 2 336 434. Aug. 1977.

English language Derwent Abstract of FR 2 368 508. Jun. 1978.

English language Derwent Abstract of FR 2 383 660. Nov. 1978.

English language Derwent Abstract of FR 2 633 940. Jan. 1990.

English language Derwent Abstract of FR 2 769 221. Apr. 1999.

* cited by examiner

ANHYDROUS COMPOSITION FOR BLEACHING KERATIN FIBERS COMPRISING A COMBINATION OF A WATER-SOLUBLE THICKENING POLYMER AND A NONIONIC AMPHIPHILIC POLYMER COMPRISING AT LEAST ONE FATTY CHAIN

The present invention relates to anhydrous compositions for bleaching keratin fibers, comprising a combination of at least one nonionic amphiphilic polymer comprising at least one fatty chain, and at least one water-soluble thickening polymer. The present invention also relates to the use of these compositions for preparing ready-to-use bleaching compositions, to a process for bleaching keratin fibers using these compositions, and to a packaging kit containing such a composition.

Bleaching powders containing a peroxygenated reagent, such as ammonium or alkali metal persulphates, perborates or percarbonates, which are combined with an aqueous hydrogen peroxide composition at the time of use are generally used for bleaching the hair. Since peroxygenated salts and hydrogen peroxide are relatively stable in acidic medium, it is necessary to activate them at basic pH in order to obtain an adequate formation of oxygen. It is thus common to add alkaline compounds such as amines and alkaline silicates to bleaching powders.

In the field of hair bleaching, bleaching compositions are generally sought which are thick enough to allow a precise application onto certain regions of the head of hair, and which do not run the risk of running onto the face or beyond the regions which it is proposed to bleach.

The thickening or gelling effect is conventionally obtained with traditional thickeners such as cellulose derivatives, starch derivatives, alginates or thickening silicates.

However, when these traditional thickeners are used, there is a large decrease in the viscosity of the final bleaching composition over time.

Thus, there is a need for a thickening system capable of maintaining a high viscosity for the time required to obtain the desired bleaching effect, which is generally between ten minutes and one hour.

The Inventors have discovered, surprisingly, that it is possible to considerably improve the maintenance of the viscosity over time of bleaching compositions by combining the conventional water-soluble thickeners with a nonionic amphiphilic polymer comprising at least one fatty chain.

It has also been found that such a thickening system allows much larger dilutions, with aqueous hydrogen peroxide compositions, than the known thickening systems.

Consequently, one subject of the present invention is an anhydrous composition for bleaching keratin fibers, in particular human keratin fibers, comprising, in a medium which is suitable for bleaching, at least one alkaline agent, at least one peroxygenated salt and, in addition, a combination
- of at least one water-soluble thickening polymer, and
- of at least one nonionic amphiphilic polymer comprising at least one fatty chain.

A subject of the invention is also the use of such a composition to prepare a ready-to-use bleaching composition.

A further subject of the invention is a process for bleaching keratin fibers using the anhydrous bleaching composition described above, as well as a packaging kit containing such a composition.

Other subjects of the invention will become apparent on reading the description and the examples which follow.

The water-soluble thickening polymers which can be used according to the present invention encompass all the synthetic water-soluble polymers or those of natural origin which are conventionally used in cosmetics.

Examples of synthetic thickening polymers which may be mentioned, for example, are polyvinylpyrrolidone, polyacrylic acid, polyacrylamide, polyacrylamidomethylpropanesulphonic acid or copolymers thereof, these polymers being crosslinked or non crosslinked.

The thickening polymers of natural origin, which can be used according to the present invention, are polymers comprising at least one sugar unit, namely (a) nonionic guar gums;
(b) biopolysaccharide gums of microbial origin such as scleroglucan gum and xanthan gum;
(c) gums derived from plant exudates such as gum arabic, ghatti gum, karaya gum or gum tragacanth;
(d) gums extracted from algae, such as carrageenans or agar;
(e) gums obtained from plant extracts, such as carob gum or pectins extracted from fruit pulp;
(f) alginates;
(g) starches; and
(h) hydroxyalkylcelluloses and carboxyalkylcelluloses.

In the present invention, the expression "sugar unit" means a monosaccharide moiety or an oligo- or polysaccharide moiety comprising the same type of saccharide units (oligo- or polyholosides) or of several types of different saccharide units (oligo- or polyheterosides).

The saccharide units of all these polymers can bear one or more substituents, for example alkyl, hydroxyalkyl, alkoxy, acyloxy or carboxyl groups, the alkyl radicals comprising from 1 to 4 carbon atoms.

The nonionic guar gums can be modified or unmodified. The unmodified guar gums are, for example, products sold under the name VIDOGUM GH 175 by the company Unipectine and under the name JAGUAR C by the company Mayhall.

According to the present invention, it is also possible to use nonionic guar gums modified with ($C_1$–$C_4$)hydroxyalkyl groups, for example hydroxymethyl, hydroxyethyl, hydroxypropyl and hydroxybutyl groups.

These modified guar gums are well known in the art and can be prepared by reacting guar gum with suitable alkylene oxides. The degree of hydroxyalkylation (ratio of the number of alkylene oxide molecules fixed to the initial number of free hydroxyl groups) is preferably from 0.4 tol 0.2.

Such modified nonionic guar gums are sold, for example, under the names JAGUAR HP8, JAGUAR HP60, JAGUAR HP120, JAGUAR DC293 and JAGUAR HP105 by the company Rhône-Poulenc (Mayhall) or under the name GALACTASOL 4H4FD2 by the company Aqualon.

The biopolysaccharide gums of microbial origin, such as scleroglucan gum or xanthan gum; the gums obtained from plant exudates, such as gum arabic, ghatti gum, karaya gum or gum tragacanth; the algal extracts, such as carrageenans or agar; the plant extracts, such as carob gum or pectins; the alginates; the starches and the hydroxyalkylcelluloses and carboxyalkylcelluloses are well known in the art and are described in particular in the "Handbook of Water Soluble Gums and Resins" by Robert L. Davidson, published by McGraw Hill Book Company (1980), the disclosure of which is hereby incorporated by reference.

Among these gums, the scleroglucans are represented by the products sold by the company Sanofi Bio Industries under the name ACTIGUM CS, and in particular under the name ACTIGUM CS 11, and by the company Alban Muller International under the name AMIGEL.

It is also possible to use other scleroglucans, for example a scleroglucan treated with glyoxal described in patent application FR-A-2 633 940, the disclosure of which is hereby incorporated by reference.

The xanthan gums which can be used as thickeners in the compositions of the present invention are represented, for example, by the products sold under the names KELTROL, KELTROL T, KELTROL TF, KELTROL BT, KELTROL RD and KELTROL CG by the company Nutrasweet Kelco, or under the names RHODICARE S or RHODICARE H by the company Rhodia Chimie.

The hydroxyalkylcelluloses are generally hydroxy($C_1$–$C_4$ alkyl)celluloses and more particularly hydroxyethylcelluloses. They are available, for example, under the names CELLOSIZE QP3L, CELLOSIZE QP4400H, CELLOSIZE QP30000H, CELLOSIZE HEC30000A or CELLOSIZE Polymer PCG10 by the company Amerchol, under the names NATROSOL 250HHR, NATROSOL 250MR, NATROSOL 250M, NATROSOL 250HHXR, NATROSOL 250HHX, NATROSOL 250HR or NATROSOL HX by the company Hercules or under the name TYLOSE H1000 by the company Hoechst.

The hydroxyalkylcelluloses can also be hydroxypropylcelluloses sold under the names KLUCEL EF, KLUCEL H, KLUCEL LHF, KLUCEL MF or KLUCEL G by the company Aqualon.

Among the carboxyalkylcelluloses which are preferably used is the carboxymethylcellulose which is sold, for example, under the names BLANOSE 7M8/SF, BLANOSE RAFFINÉE 7M, BLANOSE 7LF, BLANOSE 7MF, BLANOSE 9M31F, BLANOSE 12M31XP, BLANOSE 12M31P, BLANOSE 9M31XF, BLANOSE 7H, BLANOSE 7M31 or BLANOSE 7H3SXF by the company Aqualon, under the names AQUASORB A500 and AMBERGUM 1221 by the company Hercules, under the names CELLOGEN HP810A and CELLOGEN HP6HS9 by the company Montello or under the name PRIMELLOSE by the company Avebe.

The water-soluble thickening polymers which can be used particularly preferably as conventional thickeners in the anhydrous bleaching composition of the present invention are guar gums, guar gum derivatives or hydroxyalkylcelluloses.

The water-soluble thickener(s) described above is(are) generally used in a proportion of from 0.03 to 30% by weight, preferably a proportion of from 0.3 to 15% by weight, relative to the anhydrous composition.

In order to obtain the advantageous rheological properties indicated above, i.e., a viscosity which is high and stable over time, even for large dilutions, it is necessary according to the present invention to add to the water-soluble thickening polymers described above nonionic amphiphilic polymers comprising at least one fatty chain.

The nonionic amphiphilic polymers comprising at least one fatty chain which can be used according to the present invention encompass, for example:

celluloses or hydroxyalkylcelluloses modified with groups comprising at least one fatty chain, such as an alkyl, arylalkyl or alkylaryl group containing an alkyl group which is preferably ($C_8$–$C_{22}$), such as the products NATROSOL PLUS GRADE 330 CS from the company Aqualon, BERMOCELL EHM 100 from the company Berol Nobel, or POLYSURF 67 from the company Hercules, or modified with polyalkoxylated alkylphenol groups, such as the product AMERCEL POLYMER HM-1500 from the company Amerchol;

hydroxypropyl guars modified with groups comprising at least one ($C_8$–$C_{22}$) fatty chain such as the products ESAFLOR HM 22 ($C_{22}$ alkyl chain) from the company Lamberti, or MIRACARE $XC_{95}$-3 ($C_{14}$ alkyl chain) and RE205-1 ($C_{20}$ alkyl chain) from the company Rhône-Poulenc;

polyurethanes comprising at least one fatty chain of ($C_8$–$C_{30}$) alkyl or alkenyl type such as SER-AD FX 1100 from the company Servo Delben;

the SMDI (saturated methylene diphenyl diisocyanate) polyethylene glycol(s) copolymer with a decyl end group;

the SMDI (saturated methylene diphenyl diisocyanate) polyethylene glycol(s) copolymer with an alkyl (methyl/$C_{18}$) end group, combined with a maltodextrin matrix, or;

the HMDI (hexamethylene diisocyanate) diurethane of oxyethylenated (66 EO) and oxypropylenated (14 PO) ($C_{10}$–$C_{18}$) alcohols, sold under the name ELFACOS T 212 by the company Akzo;

copolymers of vinylpyrrolidone and of hydrophobic monomers containing a fatty chain, such as the products ANATRON V216 or GANEX V216 (poly(vinylpyrrolidone/hexadecene)), ANATRON V220 or GANEX V220 (poly(vinylpyrrolidone/eicosene)) from the company ISP;

copolymers of ($C_1$–$C_6$) alkyl (meth)acrylates and of amphiphilic monomers comprising at least one fatty chain;

copolymers of hydrophilic (meth)acrylates and of hydrophobic monomers comprising at least one fatty chain, for example a poly(polyethylene glycol methacrylate/lauryl methacrylate).

Polyurethanes comprising at least one fatty chain of ($C_{10}$–$C_{20}$) alkyl type and hydroxyethylcelluloses modified with groups comprising at least one ($C_8$–$C_{22}$) alkyl radical are preferred in particular.

These nonionic amphiphilic polymers are used in a proportion of from 0.03 to 30% by weight, preferably in a proportion of from 0.3 to 15% by weight, relative to the anhydrous bleaching composition.

The weight ratio of the nonionic amphiphilic polymer comprising at least one fatty chain to the water-soluble thickening polymer is generally from 10:1 to 1:10 and preferably from 5:1 to 1:5.

The anhydrous bleaching composition of the present invention can contain, in addition to the thickening system comprising at least one water-soluble thickening polymer and at least one nonionic amphiphilic polymer comprising at least one fatty chain, at least one anionic amphiphilic polymer comprising at least one fatty chain.

When they are present, these anionic amphiphilic polymers also act as thickeners and can reinforce the effect of the thickening system described above.

The polymers are usually crosslinked or non-crosslinked synthetic copolymers comprising hydrophilic units derived from one or more monomers containing ethylenic unsaturation bearing a free carboxylic acid function, and hydrophobic units derived from one or more monomers containing ethylenic unsaturation bearing a hydrophobic side chain, and optionally crosslinking units derived from one or more polyunsaturated monomers.

The monomer(s) containing ethylenic unsaturation bearing a carboxylic acid function is(are) chosen from ethacrylic acid, methacrylic acid and acrylic acid, preferably from methacrylic acid and acrylic acid and mixtures thereof.

The monomer(s) containing ethylenic unsaturation bearing a hydrophobic side chain can be (i) fatty alkyl esters of unsaturated carboxylic acids, or (ii) allyl fatty alkyl ethers.

(i) The fatty alkyl esters of unsaturated carboxylic acids are chosen, for example, from ($C_{10}$–$C_{30}$), preferably ($C_{12}$–$C_{22}$), alkyl ethacrylates, methacrylates and/or acrylates.

They encompass, for example, lauryl acrylate, stearyl acrylate, decyl acrylate, isodecyl acrylate and dodecyl acrylate, as well as the corresponding methacrylates, i.e. lauryl methacrylate, stearyl methacrylate, decyl methacrylate, isodecyl methacrylate and dodecyl methacrylate.

(ii) The allyl fatty alkyl ethers forming the hydrophobic units of the anionic amphiphilic polymers of the present invention correspond to the formula:

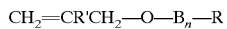

$$CH_2=CR'CH_2-O-B_n-R \qquad (I)$$

in which

R' is a hydrogen atom or a methyl group,

B is an ethylenoxy group, n is an integer ranging from 0 to 100,

R is a hydrocarbon-based group chosen from alkyl, arylalkyl, aryl, alkylaryl and cycloalkyl residues comprising from 8 to 30 carbon atoms, preferably from 10 to 24 carbon atoms, and more particularly from 12 to 18 carbon atoms.

One unit of formula (I) which is preferred, according to the present invention, is a unit in which R' denotes a hydrogen atom, n is equal to 10 and R represents a stearyl ($C_{18}$) radical.

The crosslinking monomer is a compound comprising at least two non-conjugated polymerizable double bonds. Examples or which may include, but are not limited to, diallyl phthalate, allyl (meth)acrylate, divinylbenzene, (poly)ethylene glycol dimethacrylate, methylenebisacrylamide, polyallylsucrose or polyallylpentaerythritol.

Anionic amphiphilic polymers of the type described above are described, for example, in U.S. Pat. Nos. 3,915,921 and 4,509,949 (copolymers of (eth/meth)acrylic acid and of ($C_{10}$–$C_{30}$) alkyl (eth/meth)acrylates), or in patent EP-0 216 479 B2, (copolymers of (eth/meth)acrylic acid and of allyl fatty alcohol ethers), the disclosures of which are hereby incorporated by reference.

Examples of preferred polymers may include, but are not limited to:

crosslinked polymers of acrylic acid and of ($C_{10}$–$C_{30}$) alkyl acrylate, such as the polymers sold under the names PEMULEN TR1, PEMULEN TR2 and CARBOPOL 1382 by the company Goodrich, the crosslinked polymer of acrylic acid and of ($C_{10}$–$C_{30}$) alkyl methacrylate, such as CARBOPOL ETD 2020 sold by the company Goodrich, the oxyethylenated methacrylic acid/ethyl acrylate/stearyl methacrylate (55/35/10) terpolymer, the oxyethylenated (25 EO) (meth)acrylic acid/ethyl acrylate/behenyl methacrylate terpolymer, and the crosslinked methacrylic acid/ethyl acrylate/steareth-10 allyl ether terpolymer.

These anionic amphiphilic polymers are present, where necessary, in the anhydrous bleaching compositions of the invention in a proportion of from 0.03 to 30% of the total weight of the composition.

As indicated above, the anhydrous bleaching composition contains at least one alkaline agent and at least one peroxygenated salt.

The alkaline agent is chosen from ammonium salts such as ammonium chloride, sulphate, phosphate or nitrate, and alkali metal or alkaline-earth metal silicates, phosphates or carbonates, in particular alkali metal metasilicates.

The peroxygenated salts are chosen from the ammonium or alkali metal persulphates, percarbonates and perborates.

Persulphates are preferably used, and among these sodium persulphate and potassium persulphate are mainly used.

The compositions of the invention comprise from 20 to 70% by weight and preferably from 30 to 60% by weight of peroxygenated salt(s) relative to the total weight of the anhydrous composition.

The anhydrous bleaching compositions of the present invention can also contain bleaching adjuvants of any kind capable of facilitating the handling and application, of improving the storage and efficacy of the compositions and of improving the cosmetic properties of the treated hair.

These adjuvants are, for example, agents for controlling the release of oxygen, such as magnesium carbonate and magnesia; anionic, nonionic, cationic, amphoteric or zwitterionic surfactants and mixtures thereof; mineral or plant oils; waxes; granulating adjuvants; binders; mineral fillers such as silica and clay; opacifiers such as titanium oxide; dyes; sequestering agents; fragrances and cationic or amphoteric substantive polymers.

Needless to say, a person skilled in the art will take care to select this or these optional additional compounds and the amount thereof such that the advantageous properties intrinsically associated with the bleaching composition in accordance with the invention are not, or are not substantially, adversely affected by the addition(s) envisaged.

The cationic substantive polymers, which can be used in accordance with the present invention, can be chosen from any of those already known per se as improving the cosmetic properties of the hair, namely, in particular, those described in patent applications EP-A-337354 and EP-A-557203 and in French patents FR-2 270 846, 2 383 660, 2 598 611, 2 470 596 and 2 519 863, the disclosures of all of which are hereby incorporated by reference.

The preferred cationic polymers are chosen from those which contain units comprising primary, secondary, tertiary and/or quaternary amine groups which can either form part of the main polymer chain or can be borne by a side substituent directly linked thereto.

The cationic polymers generally used have a number-average molecular mass of from 500 to $5 \times 10^6$ approximately, and preferably from 1000 to $3 \times 10^6$ approximately.

Among the cationic substantive polymers which can be mentioned more particularly are polymers such as polyamine, polyamino amide and polyquaternary ammonium.

These are known products. They are described in particular in French Patents Nos. 2 505 348 and 2 542 997, the disclosures of both of which are hereby incorporated by reference. Among the said polymers which may be mentioned are:

(1) homopolymers or copolymers derived from acrylic or methacrylic esters or amides and comprising at least one of the units of formula (II), (III), (IV) or (V) below:

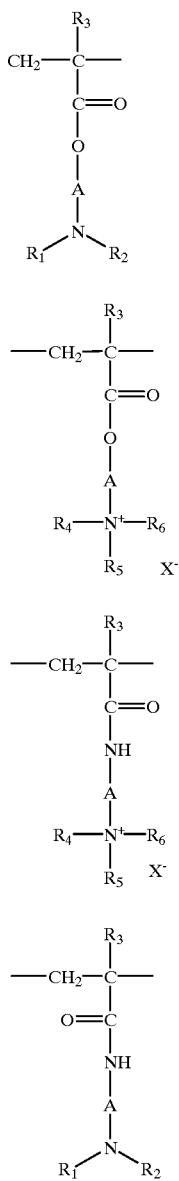

in which:
R$_3$, which may be identical or different, is chosen from a hydrogen atom or a CH$_3$ radical;
A, which may be identical or different, is chosen from a linear or branched alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, are chosen from an alkyl group containing from 1 to 18 carbon atoms or a benzyl radical, and preferably an alkyl group containing from 1 to 6 carbon atoms;
R$_1$ and R$_2$, which may be identical or different, are chosen from hydrogen or an alkyl group containing from 1 to 6 carbon atoms, and preferably methyl or ethyl;
X is chosen from an anion derived from an inorganic or organic acid, such as a methosulphate anion or a halide such as chloride or bromide.

The polymers of family (1) can also contain one or more units derived from comonomers which can be chosen from the family of acrylamides, methacrylamides, diacetone acrylamides, acrylamides and methacrylamides substituted on the nitrogen with lower (C$_1$–C$_4$) alkyls, acrylic or methacrylic acids or esters thereof, vinyllactams such as vinylpyrrolidone or vinylcaprolactam, and vinyl esters.

Thus, among these polymers of family (1) which may be mentioned are:

copolymers of acrylamide and of dimethylaminoethyl methacrylate quaternized with dimethyl sulphate or with a dimethyl halide, copolymers of acrylamide and of methacryloyloxyethyl-trimethylammonium chloride described, for example, in patent application EP-A-080976, the disclosure of which is hereby incorporated by reference, the copolymer of acrylamide and of methacryloyloxyethyltrimethylammonium methosulphate, quaternized or non-quaternized vinylpyrrolidone/ dialkylaminoalkyl acrylate or methacrylate copolymers. These polymers are described in detail in French patents 2 077 143 and 2 393 573, the disclosures of both of which are hereby incorporated by reference, dimethylaminoethyl methacrylate/vinylcaprolactam/ vinylpyrrolidone terpolymers, vinylpyrrolidone/methacrylamidopropyidimethylamine copolymers, and quaternized vinylpyrrolidone/ dimethylaminopropylmethacrylamide copolymers.

(2) The cellulose ether derivatives containing quaternary ammonium groups, described in French patent 1,492,597, the disclosure of which is hereby incorporated by reference. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, the disclosure of which is hereby incorporated by reference, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

(4) The cationic polysaccharides described more particularly in U.S. Pat. Nos. 3,589,578 and 4,031,307, the disclosures of both of which are hereby incorporated by reference, such as guar gums containing cationic trialkylammonium groups. Guar gums modified with a salt (e.g. chloride) of 2,3-epoxypropyltrimethylammonium are used, for example.

(5) Polymers comprising piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361, the disclosures of both of which are hereby incorporated by reference.

(6) Water-soluble polyamino amides prepared in particular by polycondensation of an acidic compound with a polyamine. These polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyidiamine, a bis-alkyl halide, an epihalohydrin, a diepoxide or a bis-unsaturated derivative. The crosslinking agent is used in proportions ranging from 0.025 to 0.35 mol per amine group of the polyamino amide. These polyamino amides can be alkylated or, if they contain one or more tertiary amine functions, they can be quaternized. Such polymers are described, in particular, in French patents 2,252,840 and 2,368,508, the disclosures of both of which are hereby incorporated by reference.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363, the disclosure of which is hereby incorporated by reference.

Among these derivatives, mention may be made more particularly of the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1. The polyamino amide resulting therefrom is reacted with epichlorohydrin in a molar ratio of epichlorohydrin relative to the secondary amine group of the polyamino amide of from 0.5:1 to 1.8:1. Such polymers are described in particular in U.S. Pat. Nos. 3,227,615 and 2,961,347, the disclosures of both of which are hereby incorporated by reference.

(9) Cyclopolymers of alkyldiallylamine or of dialkyldiallylammonium, such as the homopolymers or copolymers containing, as main constituent of the chain, units corresponding to formula (VI) or (VII):

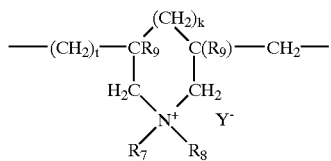

(VI)

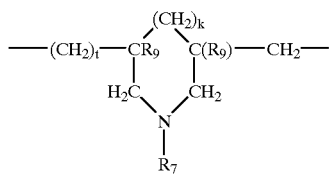

(VII)

in which:
formulae k and t are equal to 0 or 1, the sum k+t being equal to 1;
$R_9$ is chosen from a hydrogen atom or a methyl radical;
$R_7$ and $R_8$, independently of each other, are chosen from an alkyl group having from 1 to 22 carbon atoms, a hydroxyalkyl group in which the alkyl group preferably has 1 to 5 carbon atoms, or a lower ($C_1$–$C_4$) amidoalkyl group, or $R_7$ and $R_8$ can denote, together with the nitrogen atom to which they are attached, heterocyclic groups such as piperidyl or morpholinyl;

$Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406, the disclosures of which are hereby incorporated by reference.

(10) The quaternary diammonium polymer containing repeating units corresponding to the formula:

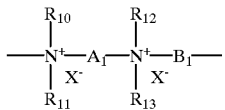

(VIII)

in which:
$R_{10}$, $R_{11}$, $R_{12}$ and $R_{13}$, which may be identical or different, are chosen from aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ are chosen from a linear or branched ($C_1$–$C_6$) alkyl radical substituted with a nitrile, ester, acyl or amide group or a group —CO—O—$R_{14}$—D or —CO—NH—$R_{14}$—D where $R_{14}$ is an alkylene and D is a quaternary ammonium group;

$A_1$ and $B_1$ are chosen from polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ is chosen from an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group

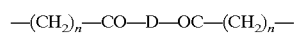

in which:
n is an integer ranging from 1 to 100 and preferably from 1 to 50, and D is chosen from:
a) a glycol residue of formula:
—O—Z—O—, where Z is chosen from a linear or branched hydrocarbon radical or a group corresponding to one of the following formulae:

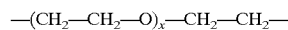

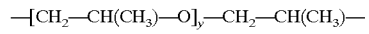

where x and y are chosen from an integer ranging from 1 to 4, representing a defined and unique degree of polymerization or any number from 1 to 4 representing an average degree of polymerization;

b) a bis-secondary diamine residue such as a piperazine derivative;
c) a bis-primary diamine residue of formula: —NH—Y—NH—, where Y denotes a linear or branched hydrocarbon radical, or alternatively the divalent radical

—CH$_2$—CH$_2$—S—S—CH$_2$—CH$_2$—;

d) a ureylene group of formula: —NH—CO—NH—.

Preferably, X$^-$ is an anion such as chloride or bromide.

These polymers generally have a number-average molecular mass ranging from 1000 to 100,000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of all of which are hereby incorporated by reference.

Polymers which can be used more particularly are those comprising repeating units corresponding to formula (IX) below:

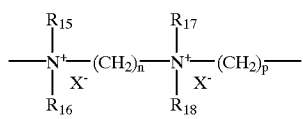

(IX)

in which:

R$_{15}$, R$_{16}$, R$_{17}$ and R$_{18}$, which may be identical or different, are chosen from an alkyl or hydroxyalkyl radical containing from 1 to 4 carbon atoms approximately;

n and p are integers ranging from 2 to 20 approximately; and

X$^-$ is an anion derived from an inorganic or organic acid.

(11) Polyquaternary ammonium polymers comprising units of formula (X):

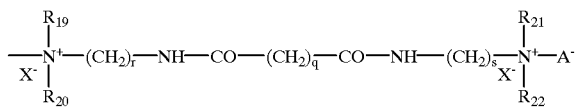

(X)

in which formula:

R$_{19}$, R$_{20}$, R$_{21}$ and R$_{22}$, which may be identical or different, are chosen from a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer ranging from 1 to 6, with the proviso that R$_{19}$, R$_{20}$, R$_{21}$ and R$_{22}$ do not simultaneously represent a hydrogen atom, r and s, which may be identical or different, are integers ranging from 1 to 6, q is equal to 0 or to an integer ranging from 1 to 34, X denotes a halogen atom, A denotes a dihalide radical or preferably represents —CH$_2$—CH$_2$—O—CH$_2$—CH$_2$—.

Such compounds are described in particular in patent application EP-A-122,324, the disclosure of which is hereby incorporated by reference.

(12) Quaternary polymers of vinylpyrrolidone and of vinylimidazole.

(13) Polyamines such as the product referred to under the name Polyethylene glycol (15) tallow polyamine in the CTFA dictionary.

(14) Crosslinked polymers of methacryloyloxy (C$_1$–C$_4$) alkyltri(C$_1$–C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing olefinic unsaturation, in particular methylenebisacrylamide. It is more particularly possible to use an acrylamide/methacryloyloxyethyltrimethylammonium chloride (20/80 by weight) crosslinked copolymer in the form of a dispersion containing 50% by weight of the said copolymer in mineral oil. This dispersion is sold under the name SALCARE® SC 92 by the company Allied Colloids. It is also possible to use a crosslinked homopolymer of methacryloyloxyethyltrimethylammonium chloride containing about 50% by weight of the homopolymer in mineral oil or in a liquid ester. These dispersions are sold under the names SALCARE® SC 95 and SALCARE® SC 96 by the company Allied Colloids.

Other cationic substantive polymers, which can be used in the context of the invention, are polyalkyleneimines, in particular polyethyleneimines, polymers containing vinylpyridine or vinylpyridinium units, condensates of polyamines and epichlorohydrin, polyquaternary ureylenes and chitin derivatives.

The amphoteric substantive polymers, which can be used in accordance with the present invention, can be chosen from polymers containing units K and M distributed randomly in the polymer chain, in which K is chosen from a unit derived from a monomer containing at least one basic nitrogen atom and M is chosen from a unit derived from an acid monomer containing one or more carboxylic or sulphonic groups, or alternatively K and M can be chosen from groups derived from carboxybetaine or sulphobetaine zwitterionic monomers;

K and M can also can be chosen from a cationic polymer chain containing primary, secondary, tertiary or quaternary amine groups, in which at least one of the amine groups bears a carboxylic or sulphonic group connected via a hydrocarbon radical or alternatively K and M form part of a chain of a polymer containing an α,β-dicarboxylic ethylene unit in which one of the carboxylic groups has been made to react with a polyamine containing one or more primary or secondary amine groups.

The amphoteric film-forming polymers corresponding to the definition given above are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537, the disclosure of which is hereby incorporated by reference. Mention may also be made of the sodium acrylate/acrylamidopropyltrimethylammonium chloride copolymer.

The vinyl compound can also be a dialkyldiallylammonium salt such as diethyidiallylammonium chloride.

(2) polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides, which are more particularly preferred according to the invention, are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymer whose CTFA (4th edition, 1991), the disclosure of which is hereby incorporated by reference, name is octylacrylamide/acrylates/butylaminoethyl methacrylate copolymer is particularly used.

(3) crosslinked and alkylated polyamino amides partially or totally derived from polyamino amides of general formula:

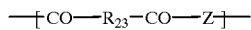

(XI)

in which:
$R_{23}$ is chosen from a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the said acids to a bis(primary) or bis(secondary) amine, and Z is chosen from a bis(primary), mono- or bis(secondary) polyalkylene-polyamine radical and preferably represents:
a) in proportions of from 60 to 100 mol %, the radical

(XII)

where x=2 and p=2 or 3, or alternatively x=3 and p=2, this radical being derived from diethylenetriamine, from triethylenetetraamine or from dipropylenetriamine;
b) in proportions of from 0 to 40 mol %, the radical (XII) above in which x=2 and p=1 and which is derived from ethylenediamine, or the radical derived from piperazine:

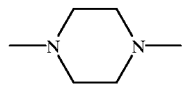

c) in proportions of from 0 to 20 mol %, the —NH—$(CH_2)_6$—NH— radical derived from hexamethylenediamine. These polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid; terephthalic acid; acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) polymers containing zwifterionic units of formula:

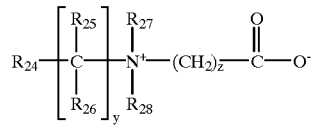

(XIII)

in which:
$R_{24}$ is chosen from a polymerizable unsaturated group such as an acrylate, methacrylate, acrylamide or methacrylamide group;
y and z are chosen from an integer ranging from 1 to 3;
$R_{25}$ and $R_{26}$ are chosen from a hydrogen atom, and methyl, ethyl and propyl radicals;
$R_{27}$ and $R_{28}$ are chosen from a hydrogen atom or an alkyl radical such that the sum of the carbon atoms in $R_{27}$ and $R_{28}$ does not exceed 10.

The polymers comprising such units can also contain units derived from non-zwitterionic monomers such as dimethyl- or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate.

(5) polymers derived from chitosan containing monomer units corresponding to formulae (XIV), (XV) and (XVI) below:

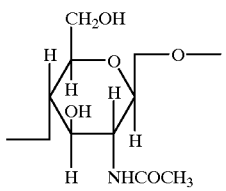

(XIV)

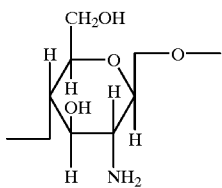

(XV)

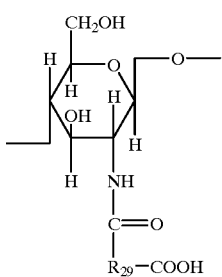

(XVI)

the unit (XIV) being present in proportions of ranging from 0 to 30%, the unit (XV) in proportions of ranging from 5 to 50% and the unit (XVI) in proportions of ranging from 30 to 90%. It being understood that, in unit (XVI), $R_{29}$ is chosen from a radical of formula:

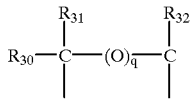

(XVII)

in which:

if q=0, $R_{30}$, $R_{31}$ and $R_{32}$, which may be identical or different, each are chosen from a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{30}$, $R_{31}$ and $R_{32}$ being, in this case, a hydrogen atom;

or, if q=1, $R_{30}$, $R_{31}$ and $R_{32}$ each are chosen from a hydrogen atom, as well as the salts formed by these compounds with bases or acids.

(6) polymers derived from the N-carboxyalkylation of chitosan, such as N-carboxymethylchitosan or N-carboxybutylchitosan.

(7) polymers corresponding to the general formula (XVIII) as are described, for example, in French patent 1,400,366, the disclosure of which is hereby incorporated by reference:

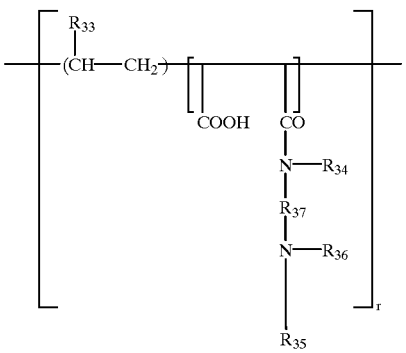

(XVIII)

in which:

r is an integer chosen such that the molecular mass of the final polymer ranges from 500 to 5,000,000 and preferably from 1000 to 3,000,000, $R_{33}$ is chosen from a hydrogen atom, a $CH_3O$, $CH_3CH_2O$ or phenyl radical;

$R_{34}$ is chosen from a hydrogen or a lower alkyl radical such as methyl or ethyl;

$R_{35}$ is chosen from hydrogen or a lower alkyl radical such as methyl or ethyl;

$R_{36}$ is a lower alkyl radical such as methyl or ethyl or a radical corresponding to the formula: $—R_{37}—N(R_{35})_2$;

$R_{37}$ is chosen from a $—CH_2—CH_2—$, $—CH_2—CH_2—CH_2—$ or $—CH_2—CH(CH_3)—$ group;

wherein $R_{35}$ has the meanings mentioned above, as well as the higher homologues of these radicals and containing up to 6 carbon atoms.

(8) amphoteric polymers of the type —D—X—D—X chosen from:

a) polymers obtained by the action of chloroacetic acid or sodium chloroacetate on compounds containing at least one unit of formula:

$$—D—X—D—X—D— \quad (XIX)$$

where D denotes a radical

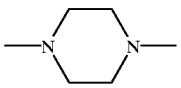

and X denotes the symbol E or E', E or E', which may be identical or different, is chosen from a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

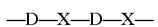 (XX)

in which D denotes a radical

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

Among the cationic or amphoteric substantive polymers which can be used according to the invention, those which are preferred in particular are:

the dimethyldiallylammonium chloride homopolymer sold under the name MERQUAT 100 DRY by the company Merck;

the copolymers of dimethyidiallylammonium chloride and of acrylamide sold under the name MERQUAT 2200 by the company Calgon;

the polymers of poly(quaternary ammonium) type prepared and described in French patent 2 270 846, the disclosure of which is hereby incorporated by reference, comprising repeating units corresponding to formula (XXI) below:

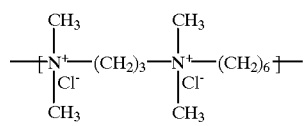 (XXI)

and in particular those whose weight-average molar mass, determined by gel permeation chromatography, ranges from 9500 to 9900;

the polymers of poly(quaternary ammonium) type prepared and described in French patent 2 270 846, the disclosure of which is hereby incorporated by reference, comprising repeating units corresponding to the formula (XXII) below:

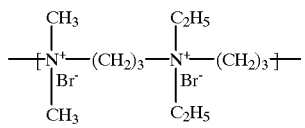 (XXII)

and in particular those whose weight-average molar mass, determined by gel permeation chromatography, is about 1200;

the polymers of poly(quaternary ammonium) type described in U.S. Pat. Nos. 4,390,689, 4,702,906 and 4,719,282, the disclosures of all of which are hereby incorporated by reference, and comprising repeating units corresponding to formula (XXIII) below:

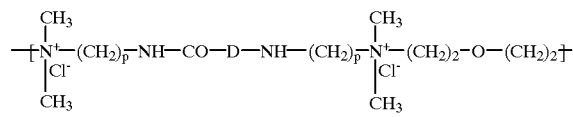 (XXIII)

in which:
p is an integer ranging from 1 to 6,
D is chosen from a single bond or a group —($CH_2$)$_r$— CO— in which r is 4 or 7, and in particular those whose weight-average molar mass is less than 100,000, preferably less than or equal to 50,000;

the following amphoteric copolymers:
the diallyidimethylammonium chloride/acrylic acid (80/20) copolymer sold under the name MERQUAT 280 DRY by the company Calgon (CTFA name: Polyquaternium-22);
the dimethyidiallylammonium chloride/acrylic acid (95/5) copolymer sold under the name MERQUAT 295 DRY by the company Calgon (CTFA name: Polyquaternium-22);
the copolymer of methacrylamidopropyltrimonium chloride, of acrylic acid and or methyl acrylate, sold under the name MERQUAT 2001 by the company Calgon (CTFA name: Polyquaternium-47); and
the acrylamide/dimethyldiallylammonium chloride/acrylic acid terpolymer sold under the name MERQUAT PLUS 3330 DRY by the company Calgon (CTFA name: Polyquaternium-39).

In the above list of substantive polymers, the amphoteric copolymers Polyquaternium-22, Polyquaternium-39 and Polyquaternium-47 (CTFA names) are preferred most particularly.

According to the invention, the cationic or amphoteric substantive polymer(s) can represent from 0.03% to 30% of the total weight of the composition.

The compositions of the invention preferably comprise at least one surfactant.

The surfactants which are suitable for carrying out the present invention are in particular the following:
(i) Anionic surfactant(s):
As examples of anionic surfactants which can be used, alone or as mixtures, in the context of the present invention, mention may be made in particular of salts (in particular alkali metal salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates and ($C_6$–$C_{24}$)acyl glutamates. It is also possible to use ($C_6$–$C_{24}$) alkylpolyglycoside carboxylic esters such as alkylglucoside citrates, alkylpolyglycoside tartrate and alkylpolyglycoside sulphosuccinates, alkyl sulphosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical comprises 8 to 20 carbon atoms. Alkyl D-galactosiduronic acids and salts thereof, polyoxyalkylenated ($C_6$–$C_{24}$)alkyl ether carboxylic acids, polyoxyalkylenated ($C_6$–$C_{24}$)alkylaryl ether carboxylic acids and polyoxyalkylenated ($C_6$–$C_{24}$)alkylamido ether carboxylic acids and salts thereof, in particular those comprising from 2 to 50 alkylene oxide groups, in particular ethylene oxide groups and mixtures thereof, can also be used.

(ii) Nonionic surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from polyethoxylated or polypropoxylated fatty acids, alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or zwitterionic surfactant(s):

The amphoteric or zwitterionic surfactants, whose nature is not a critical feature in the context of the present invention, can be, in particular aliphatic secondary or tertiary amine derivatives in which the aliphatic radical is a linear or branched chain containing 8 to 18 carbon atoms and containing at least one water-soluble anionic group (for example carboxylate, sulphonate, sulphate, phosphate or phosphonate); mention may also be made of ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido ($C_1$–$C_6$) alkylsulphobetaines.

Among the amine derivatives, mention may be made of the products described in U.S. Pat. Nos. 2,528,378 and 2,781,354 and classified in the CTFA dictionary, $3^{rd}$ edition, 1982, the disclosures of all of which are hereby incorporated by reference, under the names Amphocarboxyglycinates and Amphocarboxypropioniates, and having the respective structures:

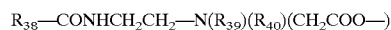

in which:

$R_{38}$ is chosen from an alkyl radical derived from an acid $R_{38}$—COOH present in hydrolyzed coconut oil, a heptyl, nonyl or undecyl radical $R_{39}$ is chosen from a β-hydroxyethyl group; and $R_{40}$ denotes a carboxymethyl group; and

in which:

B is —$CH_2CH_2OX'$,

C is —$(CH_2)_z$—Y', with z=1 or 2,

X' is chosen from a —$CH_2CH_2$—COOH group or a hydrogen atom,

Y' is chosen from a —COOH or the —$CH_2$—CHOH—$SO_3H$ radical, $R_{38}'$ is chosen from an alkyl radical of an acid $R_{38}$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, the disclosure of which is hereby incorporated by reference, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

(iv) Cationic surfactants:

Among the cationic surfactants which may be mentioned in particular are: optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can represent from 0.01 to 40% and preferably from 0.1 to 30% of the total weight of the composition.

The anhydrous bleaching composition can be in the form of a powder which produces a poultice after mixing with aqueous hydrogen peroxide solution. It can also be in the form of an anhydrous bleaching cream containing pulverulent agents suspended or dispersed in an organic solvent, such as the creams described in patents; U.S. Pat. No. 4,170,637, DE 3 814 356, DE 3 844 956, EP 0 778 020 and DE 1 972 3538, the disclosures of all of which are hereby incorporated by reference.

According to the present invention, the anhydrous bleaching composition is preferably in the form of a powder of coated, uncoated or granulated particles.

A subject of the present invention is also a process for bleaching keratin fibers, in particular human hair.

This process comprises:

mixing, immediately before use, the anhydrous bleaching composition containing at least one alkaline agent, at least one peroxygenated salt and the combination of at least one water-soluble thickening polymer and at least one nonionic amphiphilic polymer comprising at least one fatty chain and optionally an anionic amphiphilic polymer comprising at least one fatty chain with an aqueous hydrogen peroxide composition, applying the mixture to the region of keratin fibers to be bleached, leaving the mixture to stand on the fibers for a period which is sufficient to obtain the desired bleaching, this period generally ranging from 10 minutes to one hour, preferably ranging from 10 to 45 minutes, and removing the bleaching mixture by rinsing with water, followed by washing with a shampoo, and then drying.

A further subject of the invention is the use of an anhydrous bleaching composition described above to prepare a ready-to-use bleaching composition. For this, the anhydrous composition is mixed with about 0.5 to 10 equivalents by weight of an aqueous hydrogen peroxide composition, for example a solution, an emulsion or a gel with a weight concentration ranging from 2 to 12%. This mixing must be carried out immediately before applying the product to the hair.

The pH of the ready-to-use bleaching composition is preferably from 7 to 12 and even more preferably from 8.5 to 11.5.

Another subject of the invention is a packaging device in several parts, also known as a packaging "kit", comprising at least two compartments, one of which contains an anhydrous bleaching composition as described above, and the other of which contains an aqueous hydrogen peroxide composition.

The examples given below, purely by way of illustration and with no limiting nature, will allow the invention to be understood more clearly.

EXAMPLE 1

Two pulverulent bleaching compositions were prepared, one of which (composition A) contained a combination of two conventional water-soluble thickeners, i.e., hydroxyethylcellulose and a natural polymer, guar gum, and the other of which (composition B according to the invention) contained a combination of a conventional water-soluble thickener, i.e., hydroxyethylcellulose, and a nonionic amphiphilic polymer according to the invention, i.e., cetylhydroxyethylcellulose.

The table below gives the nature and the weight amounts of the ingredients in these two compositions.

| | amounts (% by weight) | |
| --- | --- | --- |
| | Composition A (prior art) | Composition B (according to the invention) |
| potassium persulphate | 35 | 35 |
| sodium persulphate | 30 | 30 |
| sodium metasilicate | 14 | 14 |
| ammonium chloride | 5 | 5 |
| EDTA | 1 | 1 |
| sodium dioctyl sulphosuccinate/ sodium benzoate | 1 | 1 |

-continued

| | amounts (% by weight) | |
| --- | --- | --- |
| | Composition A (prior art) | Composition B (according to the invention) |
| calcium stearate | 1 | 1 |
| silica | 7 | 7 |
| guar gum* | 3 | 0 |
| cetylhydroxyethylcellulose** | 0 | 3 |
| hydroxyethylcellulose*** | 3 | 3 |

*sold under the name GUARGEL D/15 by the company Société Francaise des Colloides
**sold under the name POLYSURF 67 by the company Hercules sold under the name CELLOSIZE POLYMER PCG-10 by the company Amerchol 40 g of each of the compositions A and B were mixed with 80 g of composition C below, so as to obtain two ready-to-use bleaching compositions AC and BC.

| | Composition C (amounts in % by weight) |
| --- | --- |
| cetearyl alcohol/cetearyth-30 | 2.85 |
| stabilizers | 0.06 |
| sequestering agents | 0.15 |
| hydrogen peroxide | 9 |
| phosphoric acid | qs pH 2 |
| distilled water | qs 100 |

Viscosimetric measurements over time were carried out using a rotary viscometer (Rheomat RM 180 model, from the company Mettler). All the measurements were carried out at 25° C., using a No. 3 spindle, after shear for 30 seconds at a speed of 50 s$^{-1}$.

After each measurement, composition AC or BC was homogenized by gentle stirring for a period of 1 minute.

The loss of viscosity was calculated according to the following formula:

$$\text{loss } (\%) = ((\eta_5 - \eta_t)/\eta_5) \times 100$$

in which $\eta_5$ is the viscosity measured 5 minutes after mixing compositions A and B with composition C, and $\eta_t$ is the viscosity measured after a time t (in minutes) following mixing of ions A and B with composition C.

The results obtained were as follows:

| | composition AC (prior art) | | composition BC (invention) | |
| --- | --- | --- | --- | --- |
| t(min) | viscosity (Pa.s) | loss (%) | viscosity (Pa.s) | loss (%) |
| 5 | 11.54 | | 15.85 | |
| 10 | 6.64 | 42 | 10.45 | 34 |
| 20 | 3.99 | 65 | 9.95 | 37 |
| 30 | 3.32 | 71 | 10.32 | 35 |

For composition AC corresponding to the prior art, an increasing loss of viscosity over time, which reached 70% after only 25 minutes, was observed.

For composition BC according to the present invention, the viscosity decreased by about 35% after 10 minutes but then remained constant over time.

EXAMPLE 2

The bleaching composition below, in the form of an anhydrous cream, was prepared (amounts in % by weight):

| | |
|---|---|
| isopropyl palmitate | 23 |
| mineral oil | 3 |
| potassium persulphate | 25 |
| sodium persulphate | 20 |
| sodium metasilicate | 12 |
| sodium alginate | 2 |
| ammonium chloride | 4 |
| ethylenediaminetetraacetic acid | 1 |
| cetylstearyl alcohol containing 25 mol of ethylene oxide | 2 |
| clay | 1 |
| Polyquaternium-22 | 1 |
| Serad FX-1100 | 3 |
| titanium oxide | 1 |
| magnesium stearate | 2 |

10 g of this composition were mixed with 15 g of composition C described above. This mixture was applied and maintained on hair to be bleached, for 45 minutes. Uniform bleaching was obtained after rinsing, shampooing and drying. The state of the fiber was satisfactory, with limited degradation.

The foregoing written description relates to various embodiments of the present invention. Numerous changes and modifications may be made therein without departing from the spirit and scope of the invention as defined in the following claims.

What is claimed is:

1. An anhydrous composition for bleaching keratin fibres, comprising:
   at least one alkaline agent,
   at least one peroxygenated salt,
   at least one water-soluble thickening polymer, and
   at least one nonionic amphiphilic polymer comprising at least one $C_8$–$C_{30}$ fatty chain.

2. The composition according to claim 1, wherein the keratin fibers are human keratin fibers.

3. The composition according to claim 1, wherein the at least one water-soluble thickening polymer is a polymer of natural or synthetic origin.

4. The composition according to claim 3, wherein the thickening polymer of synthetic origin is chosen from polyvinylpyrrolidone, polyacrylic acid, polyacrylamide, polyacrylamidomethylpropanesulphonic acid and copolymers thereof, these polymers being crosslinked or non-crosslinked.

5. The composition according to claim 3, wherein the thickening polymer of natural origin is chosen from
   (a) nonionic guar gums;
   (b) biopolysaccharide gums of microbial origin;
   (c) gums derived from plant exudates;
   (d) gums extracted from algae;
   (e) gums obtained from plant extracts;
   (f) alginates;
   (g) starches; and
   (h) hydroxyalkylcelluloses and carboxyalkylcelluloses.

6. The composition according to claim 5, wherein the biopolysaccharide gums of microbial origin are chosen from scleroglucan gum and xanthan gum.

7. The composition according to claim 5, wherein the gums derived from plant exudates are chosen from gum arabic, ghatti gum, karaya gum and gum tragacanth.

8. The composition according to claim 5, wherein the gums extracted from algae are chosen from carrageenans and agar.

9. The composition according to claim 5, wherein the gums obtained from plant extracts are chosen from carob gum and pectins extracted from fruit pulp.

10. The composition according to claim 5, wherein the thickening polymer of natural origin is chosen from a guar gum, a guar gum derivative or a hydroxyalkylcellulose.

11. The composition according to claim 1, wherein the at least one nonionic amphiphilic polymer comprising at least one $C_8$–$C_{30}$ fatty chain is chosen from
   celluloses or hydroxyalkylcelluloses modified with groups comprising at least one fatty chain chosen from alkyl, arylalkyl and alkylaryl fatty chains containing a ($C_8$–$C_{22}$) alkyl group, or with polyalkoxylated alkylphenol groups;
   hydroxypropyl guars modified with groups comprising at least one ($C_8$–$C_{22}$) fatty chain;
   polyurethanes comprising at least one fatty chain of ($C_8$–$C_{30}$) alkyl or alkenyl type;
   copolymers of vinylpyrrolidone and of hydrophobic monomers containing a fatty chain;
   copolymers of ($C_1$–$C_6$) alkyl (meth)acrylates and of amphiphilic monomers comprising at least one fatty chain; and
   copolymers of hydrophilic (meth)acrylates and of hydrophobic monomers comprising at least one fatty chain.

12. The composition according to claim 11, wherein the at least one nonionic amphiphilic polymer is a hydroxyethylcellulose modified with groups comprising at least one ($C_8$–$C_{22}$) alkyl radical or a polyurethane comprising at least one ($C_{10}$–$C_{20}$) alkyl chain.

13. The composition according to claim 1, wherein the at least one water-soluble thickening polymer is present in the composition in an amount ranging from 0.03 to 30% by weight relative to the total weight of the composition.

14. The composition according to claim 13, wherein the at least one water-soluble thickening polymer is present in the composition in an amount ranging from 0.3 to 15% by weight relative to the total weight of the composition.

15. The composition according to claim 1, wherein the at least one nonionic amphiphilic polymer is present in the composition in an amount ranging from 0.03 to 30% by weight relative to the total weight of the composition.

16. The composition according to claim 15, wherein the at least one nonionic amphiphilic polymer is present in the composition in an amount ranging from 0.3 to 15% by weight relative to the total weight of the composition.

17. The composition according to claim 1, wherein the at least one nonionic amphiphilic polymer comprising at least one $C_8$–$C_{30}$ fatty chain and the at least one water-soluble thickening polymer are present in a weight ratio ranging from 10:1 to :10.

18. The composition according to claim 17, wherein the weight ratio of the nonionic amphiphilic polymer comprising at least one $C_8$–$C_{30}$ fatty chain to the water-soluble thickening polymer ranges from 5:1 to 1:5.

19. The composition according to claim 1, wherein the composition also contains an anionic amphiphilic polymer comprising at least one fatty chain.

20. The composition according to claim 19, wherein the anionic amphiphilic polymer comprising at least one fatty chain is a copolymer comprising
   hydrophilic units derived from one or more monomers containing ethylenic unsaturation and bearing a carboxylic acid function, and hydrophobic units derived from one or more monomers containing ethylenic unsaturation and bearing a hydrophobic side chain.

21. The composition according to claim 20, wherein the monomers containing ethylenic unsaturation and bearing a carboxylic acid function are chosen from ethacrylic acid, methacrylic acid and acrylic acid, and mixtures thereof.

22. The composition according to claim 21, wherein the monomers containing ethylenic unsaturation and bearing a carboxylic acid function are chosen from methacrylic acid and acrylic acid.

23. The composition according to claim 20, wherein the monomers containing ethylenic unsaturation and bearing a hydrophobic side chain are chosen from ($C_{10}$–$C_{30}$) alkyl ethacrylates, methacrylates and acrylates.

24. The composition according to claim 20, wherein the monomers containing ethylenic unsaturation and bearing a hydrophobic side chain are chosen from ($C_{12}$–$C_{22}$) alkyl ethacrylates, methacrylates and acrylates.

25. The composition according to claim 20, wherein the monomers containing ethylene unsaturation and bearing a hydrophobic side chain are chosen from allyl fatty alkyl ethers corresponding to the formula:

$$CH_2=CR'CH_2-O-B_n-R \quad (I)$$

in which:
R' is chosen from a hydrogen atom and a methyl group,
B is an ethylenoxy group,
n is an integer ranging from 0 to 100,
R is a hydrocarbon-based group chosen from alkyl, arylalkyl, aryl, alkylaryl and cycloalkyl residues comprising from 8 to 30 carbon atoms.

26. The composition according to claim 25, wherein R is a hydrocarbon-based group chosen from alkyl, arylalkyl, aryl, alkylaryl and cycloalkyl residues comprising from 10 to 24 carbon atoms.

27. The composition according to claim 19, wherein the anionic amphiphilic polymer comprising at least one fatty chain also comprises units derived from a crosslinking monomer containing two non-conjugated ethylenic double bonds.

28. The composition according to claim 27, wherein the crosslinking monomer is chosen from diallyl phthalate, allyl (meth)acrylate, divinylbenzene, (poly)ethylene glycol dimethacrylate, methylenebisacrylamide, polyallylsucrose or polyallylpentaerythritol.

29. The composition according to claim 19, wherein the anionic amphiphilic polymer comprising at least one fatty chain is present in the composition in an amount ranging from 0.03 to 30% by weight relative to the total weight of the composition.

30. The composition according to claim 1, wherein the at least one alkaline agent is chosen from ammonium salts and alkali metal or alkaline-earth metal silicates, phosphates and carbonates.

31. The composition according to claim 30, wherein the ammonium salts are chosen from ammonium chloride, sulphate, phosphate or nitrate.

32. The composition according to claim 30, wherein the at least one alkaline agent is an alkali metal metasilicate.

33. The composition according to claim 1, wherein the at least one peroxygenated salt is chosen from ammonium and alkali metal persulphates, percarbonates and perborates.

34. The composition according to claim 33, wherein the at least one peroxygenated salt is chosen from sodium persulphate and potassium persulphate.

35. The composition according to claim 33, wherein the composition contains from 20 to 70% by weight of said at least one peroxygenated salt, relative to the total weight of the composition.

36. The composition according to claim 35, wherein the composition contains from 30 to 60% by weight of said at least one peroxygenated salt, relative to the total weight of the composition.

37. The composition according to claim 1, wherein the composition further comprises bleaching adjuvants chosen from agents for controlling the release of oxygen, anionic, nonionic, cationic, amphoteric or zwitterionic surfactants and mixtures thereof, mineral or plant oils, waxes, granulating adjuvants, binders, mineral fillers, opacifiers, dyes, sequestering agents, fragrances and cationic or amphoteric substantive polymers.

38. The composition according to claim 37, wherein the composition contains from 0.01 to 40% by weight of at least one surfactant, relative to the total weight of the composition.

39. The composition according to claim 38, wherein the composition contains from 0.1 to 30% by weight of at least one surfactant, relative to the total weight of the composition.

40. The composition according to claim 37, wherein the composition contains from 0.03 to 30% by weight of at least one cationic or amphoteric substantive polymer, relative to the total weight of the composition.

41. The composition according to claim 1, wherein the composition is in the form of a powder, or of a suspension or dispersion of powder in an anhydrous organic liquid support.

42. The composition according to claim 1, further comprising a medium suitable for bleaching.

43. A process for bleaching keratin fibers comprising:
mixing, immediately before application, an anhydrous bleaching composition comprising at least one alkaline agent, at least one peroxygenated salt, at least one water-soluble thickening polymer, and at least one nonionic amphiphilic polymer comprising at least one $C_8$–$C_{30}$ fatty chain, with an aqueous hydrogen peroxide composition,
applying the mixture obtained to the keratin fibers to be bleached,
leaving the mixture to stand on the fibers for a period which is sufficient to obtain the desired bleaching effect, and
removing the bleaching mixture by rinsing with water, followed by washing with a shampoo, and then drying.

44. The process according to claim 43, wherein said anhydrous bleaching composition further comprises a medium suitable for bleaching.

45. A multi-compartment device for bleaching keratin fibers comprising a first compartment and a second compartment, wherein said first compartment contains an anhydrous composition comprising at least one alkaline agent, at least one peroxygenated salt, at least one water-soluble thickening polymer, and at least one nonionic amphiphilic polymer comprising at least one $C_8$–$C_{30}$ fatty chain; and
wherein the second compartment contains an aqueous hydrogen peroxide composition.

46. The device according to claim 45, wherein the keratin fibers are human keratin fibers.

47. The device according to claim 45, wherein the human keratin fibers are hair.

48. A ready-to-use bleaching composition comprising an aqueous hydrogen peroxide composition and an anhydrous composition composition comprising at least one alkaline agent, at least one peroxygenated salt, at least one water-soluble thickening polymer, and at least one nonionic amphiphilic polymer comprising at least one fatty chain.

49. The composition according to claim 48, wherein said anhydrous composition is present in said bleaching composition in an amount ranging from 0.5 to 10 equivalents by weight of said aqueous hydrogen peroxide composition.

* * * * *

UNITED STATES PATENT AND TRADEMARK OFFICE
CERTIFICATE OF CORRECTION

PATENT NO.    : 6,379,401 B1                                              Page 1 of 1
DATED         : April 30, 2002
INVENTOR(S)   : Legrand et al.

It is certified that error appears in the above-identified patent and that said Letters Patent is hereby corrected as shown below:

Column 24,
Line 54, "to :10" should read -- to 1:10 --.

Column 27,
Line 3, delete "composition" (second occurrence).

Signed and Sealed this

Thirtieth Day of July, 2002

*Attest:*

JAMES E. ROGAN
*Attesting Officer*  *Director of the United States Patent and Trademark Office*